United States Patent
Giles et al.

(10) Patent No.: US 10,153,147 B2
(45) Date of Patent: Dec. 11, 2018

(54) METHOD OF COMPRESSING AN ION BEAM

(71) Applicant: Micromass UK Limited, Wilmslow (GB)

(72) Inventors: Kevin Giles, Stockport (GB); Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/316,025

(22) PCT Filed: Jun. 9, 2015

(86) PCT No.: PCT/GB2015/000166
§ 371 (c)(1),
(2) Date: Dec. 2, 2016

(87) PCT Pub. No.: WO2015/189538
PCT Pub. Date: Dec. 17, 2015

(65) Prior Publication Data
US 2017/0125231 A1    May 4, 2017

(30) Foreign Application Priority Data

Jun. 10, 2014   (EP) ................................ 14171725
Jun. 10, 2014   (GB) ................................ 1410247.9

(51) Int. Cl.
| H01J 49/00 | (2006.01) |
| H01J 49/06 | (2006.01) |
| H01J 49/42 | (2006.01) |
| G01N 27/62 | (2006.01) |

(52) U.S. Cl.
CPC .......... *H01J 49/066* (2013.01); *G01N 27/622* (2013.01); *H01J 49/0031* (2013.01); *H01J 49/4265* (2013.01)

(58) Field of Classification Search
CPC .. H01J 49/066; H01J 49/0031; H01J 49/4265; G01N 27/622
USPC ................................................. 250/281, 282
See application file for complete search history.

(56) References Cited

U.S. PATENT DOCUMENTS

| 5,109,157 A | 4/1992 | Loen |
| 5,189,301 A | 2/1993 | Thekkadath |
| 6,627,877 B1 | 9/2003 | Davis et al. |
| 6,717,132 B2 | 4/2004 | Franzen |
| 6,744,043 B2 | 6/2004 | Loboda |
| 7,148,474 B2 | 12/2006 | Tang et al. |
| 7,157,698 B2 | 1/2007 | Makarov et al. |
| 7,932,488 B2 | 4/2011 | Javahery et al. |

(Continued)

FOREIGN PATENT DOCUMENTS

| GB | 2274197 | 7/1994 |
| GB | 2389704 | 12/2003 |

(Continued)

*Primary Examiner* — Nicole Ippolito
*Assistant Examiner* — Hanway Chang

(57) ABSTRACT

A method of mass or ion mobility spectrometry is disclosed comprising: releasing ions from an ion trapping volume into an ion separation region; separating the ions along a longitudinal direction according to a physicochemical property; and compressing the ion beam in a direction orthogonal to the longitudinal axis. The method enables the ions to be focussed without increasing the charge density and hence space-charge effects to undesirable levels.

20 Claims, 1 Drawing Sheet

(56) References Cited

U.S. PATENT DOCUMENTS

| | | |
|---|---|---|
| 8,288,717 B2 | 10/2012 | Park |
| 8,507,848 B1 | 8/2013 | Ding et al. |
| 8,946,626 B2 | 2/2015 | Giles et al. |
| 9,053,915 B2 | 6/2015 | R1stroph et al. |
| 9,293,315 B2 | 3/2016 | Makarov |
| 9,425,034 B2 | 8/2016 | Verenchikov et al. |
| 9,466,473 B2 | 10/2016 | Giles et al. |
| 2010/0108879 A1 | 5/2010 | Bateman et al. |
| 2015/0233866 A1 | 8/2015 | Verenchikov |
| 2016/0155624 A1 | 6/2016 | Verenchikov et al. |

FOREIGN PATENT DOCUMENTS

| | | |
|---|---|---|
| GB | 2513470 | 10/2014 |
| WO | 2015189539 | 12/2015 |

METHOD OF COMPRESSING AN ION BEAM

CROSS-REFERENCE TO RELATED APPLICATIONS

This application represents the U.S. National Phase of International Application number PCT/GB2015/000166 entitled "A Method of Compressing an Ion Beam" filed 9 Jun. 2015, which claims priority from and the benefit of United Kingdom patent application No. 1410247.7 filed on 10 Jun. 2014 and European patent application No. 14171725.6 filed on 10 Jun. 2014. The entire contents of these applications are incorporated herein by reference.

FIELD OF THE INVENTION

The present invention relates to a method of mass spectrometry or ion mobility spectrometry in which an ion beam is compressed in width.

BACKGROUND

Space-charge effects can limit the performance of ion mobility spectrometers and mass spectrometers in many ways. One of the most common limitations is the ability to accumulate large populations of ions in an ion trap prior to ejection or release of the ions into a downstream analyser. Space-charge effects can be mitigated in ion traps by providing the ion trap with relatively large dimensions so as to provide a relatively large ion trapping volume. However, in order to simultaneously eject ions from such an ion trap the ions must be ejected in a packet or pulse that is relatively wide. The ion packet must then be focussed down in width so as to be transmitted through the relatively narrow differential pumping apertures that are arranged between regions of different pressures. However, this focussing compresses and concentrates the ion packet and hence reintroduces the problem of space-charge effects.

It is desired to provide an improved method of mass spectrometry or ion mobility spectrometry, and an improved mass spectrometer or ion mobility spectrometer.

SUMMARY

From a first aspect the present invention provides a method of mass spectrometry or ion mobility spectrometry comprising:

accumulating ions in an ion trapping volume;

releasing ions from the ion trapping volume into an ion separation region having a longitudinal axis, wherein the ions exit the ion trapping region distributed over an initial width in a first direction that is orthogonal to the longitudinal axis;

transmitting the ions along a longitudinal axis of the ion separation region such that the ions separate along the longitudinal axis according to a physicochemical property;

compressing the width in the first direction over which the ions are distributed whilst the ions separate along the longitudinal axis such that the ions are distributed over a width in the first direction that is smaller than or the same as said initial width; and transmitting the compressed ion beam through an ion acceptance aperture, wherein the initial width of the ion beam in the first direction is greater than the width of the aperture in the first direction, and wherein the ion beam is compressed in the first direction such that when the ions reach the aperture the ion beam has a width in the first direction that is smaller than or the same as the width of the exit aperture in the first direction.

The compression of the ion beam allows the ions to be focussed to be transmitted through a relatively small ion acceptance aperture. This compression increases the charge density of the ions at the points along the longitudinal axis that such compression takes place. However, the separation of the ions according to said physicochemical property along the longitudinal axis reduces the charge density of the ions at any given point along the longitudinal axis and hence at least partially counteracts the effect of compressing the ion beam. The present invention therefore enables the ions to be focussed without increasing the charge density and hence space-charge effects to undesirable levels.

Ion funnel arrangements are known for compressing clouds of ions into a focussed beam. However, it has not previously been recognised that ions can be focussed from large ion trapping volumes whilst mitigating space-charge effects by separating the ions prior to, or during, compression.

It is known to use a relatively wide ion mobility separator to separate ions according to their ion mobility. It is also known to funnel the ions down to a narrower ion beam after the ions have been separated, in order to transmit the separated ions into a relatively narrow downstream device. However, the step of separating the ions in order to determine their ion mobilities and the step of funneling the ions have always been considered as isolated and unrelated steps. It has not been recognised in the prior art that ion separation may be used during compression of an ion beam in order to avoid adverse space-charge effects occurring during compression.

It will be understood that the term "ion beam" as used herein may refer to a substantially continuous stream of ions that have been separated according to the physicochemical property, or may refer to one or more groups of ions that have been separated from other ions as they travel along the separation region.

The separated ions may exit the ion separation region at different exit times, and the exit times may not be used in determining the values of a physicochemical property of the ions.

From a second aspect the present invention provides a method of mass spectrometry or ion mobility spectrometry comprising:

accumulating ions in an ion trapping volume;

releasing ions from the ion trapping volume into an ion separation region having a longitudinal axis, wherein the ions exit the ion trapping region distributed over an initial width in a first direction that is orthogonal to the longitudinal axis;

transmitting the ions along a longitudinal axis of the ion separation region such that the ions separate along the longitudinal axis according to a physicochemical property; and compressing the width in the first direction over which the ions are distributed whilst the ions separate along the longitudinal axis, or after the ions have separated along the longitudinal axis, such that the ions are distributed over a width in the first direction that is smaller than or the same as said initial width;

wherein the separated ions exit the ion separation region at different exit times, and wherein the exit times are not used in determining the values of a physicochemical property of the ions.

As described above, it is known to use a relatively wide ion mobility separator to separate ions according to their ion mobility. It is also known to funnel the ions down to a narrower ion beam after the ions have been separated, in order to transmit the separated ions into a relatively narrow downstream device. However, the step of separating the ions is performed in order to determine the ion mobilities of the ions. It has not been recognised in the prior art that ion separation may be used during compression of an ion beam in order to avoid adverse space-charge effects occurring during compression. Accordingly, it is not known or obvious to separate ions and compress the ion beam in a context wherein the ion separation is not used to determine the ion mobilities of the ions.

The following features are described in relation to both the first and second aspects.

Ions may be transmitted through the ion separation region with different transit or drift times, and the transit or drift times may not be used in determining the values of a physicochemical property of the ions.

The exit times, transit times or drift times may not be used to determine the ion mobilities of the separated ions.

Said compressing may begin in the ion separation region within a distance x cm of the location at which ions are released from the ion trapping volume, wherein x is selected from the group consisting of: $\leq 100$; $\leq 90$; $\leq 80$; $\leq 70$; $\leq 60$; $\leq 50$; $\leq 40$; $\leq 30$; $\leq 20$; $\leq 10$; $\leq 5$; $\leq 4$; $\leq 3$; $\leq 2$; and $\leq 1$.

The ions may exit the ion trapping volume directly into a region in which the ions are compressed in the first direction such that the ions are compressed in the first direction immediately after they exit the ion trapping volume.

As discussed above, it has not been recognised in the prior art that ion separation may be used during compression of an ion beam in order to avoid adverse space-charge effects occurring during compression. Accordingly, it is not known to compress an ion beam released from a relatively wide ion trapping volume whilst the ions are separating and such that the compression begins at, or relatively close to, the location at which the ions are released from the ion trapping volume.

The ions may be provided to the separation region as a packet or pulse of ions. The ions may separate in the separation region into a more continuous ion beam.

The ion beam may be compressed to progressively narrower widths in the first direction as the ions travel along the longitudinal axis of the separation region.

The ion beam may be continually and progressively compressed in the first direction over y % of the length of the ion separation region, wherein y is selected from the group consisting of: >5%; >10%; >15%; >20%; >25%; >30%; >35%; >40%; >50%; >55%; >60%; >65%; >70%; >75%; >80%; >85%; >90%; and >95%.

For the avoidance of doubt, the length of the ion separation region is in the direction along the longitudinal axis.

The method may comprise accumulating ions in the ion trapping volume and then releasing, pulsing or ejecting the ions from the ion trapping volume into the separation region.

The ions are distributed over said initial width at the time they are released or pulsed from said trapping region.

The method may comprise accumulating subsequent ions in said trapping region from an upstream ion source directly after the previously trapped ions have been released or ejected from the ion trapping region and whilst they are being separated in the separation region.

The method may repeatedly perform a plurality of cycles of operation, wherein each cycle comprises accumulating ions in the ion trapping region and then pulsing the ions into the separation region.

The ions may separate along the longitudinal axis according to ion mobility or mass to charge ratio.

The separation region may be gas-filled.

The physicochemical property according to which the ions are separated in the ion separation region may be the ion mobility through a gas present in the separation region. Alternatively, the physicochemical property may be mass to charge ratio.

The method may comprise urging ions along the longitudinal axis of the separation region away from the ion trapping volume.

One or more static electric fields and/or time-varying electric fields may be used to urge the ions along the longitudinal axis. For example, a DC voltage gradient may be applied along the longitudinal axis of the separation region. Alternatively, or additionally, a DC potential barrier may be traveled along the longitudinal axis of the separation region so as to drive ions along it and towards the aperture. This may be achieved by successively applying one or more voltages to successive electrodes arranged along the longitudinal axis of the separation region. The DC barrier may be repeatedly traveled along the separation region.

Ions may be compressed in the first direction by RF and/or DC potential barriers.

An RF and/or DC field may be arranged along the longitudinal axis of the separation region for compressing said ion beam in the first direction and a characteristic of said field may vary as a function of distance along the longitudinal axis so as to cause varying amounts of compression of the ion beam along the longitudinal axis. The characteristic may, for example, be amplitude of the RF and/or DC field, or may be the frequency of the voltage used to generate the RF field.

The method of the first aspect may further comprise transmitting the compressed ion beam through an ion acceptance aperture, wherein the initial width of the ion beam in the first direction is greater than the width of the aperture in the first direction, and wherein the ion beam is compressed in the first direction such that when the ions reach the aperture the ion beam has a width in the first direction that is smaller than or the same as the width of the exit aperture in the first direction.

The ion acceptance aperture described in relation to both the first and second aspects of the invention may be an opening in a wall or electrode, e.g. an aperture in a wall between two vacuum chambers of a spectrometer. The physical boundaries of the aperture may therefore dictate the width and size of the ion acceptance aperture. Alternatively, the ion acceptance aperture may be defined by a downstream component, wherein the area of the ion acceptance aperture corresponds to the area over which ions can be accepted by the component. The width and size of the ion acceptance aperture may therefore be defined by the physical dimensions of an entrance to the component and/or by the electric potentials applied to the component.

The aperture may be a differential pumping aperture that is formed in a wall separating two regions maintained at different pressures.

The aperture may be provided in a wall and a plurality of electrodes may be arranged on the wall radially outward of the aperture in at least the first direction, wherein the method comprises applying DC and/or AC voltages to said electrodes so as to compress the ions in the first direction.

The method may comprise applying RF potentials to said electrodes so as to repel ions and prevent them contacting the wall.

The electrodes may comprise a plurality of closed-loop electrodes arranged concentrically around and radially outward of the aperture.

The electrodes may be ring-shaped, circular or another shape. The closed-loop electrodes may have the same shapes as the perimeter of the aperture.

The method may comprise applying different DC voltages to different ones of said electrodes so as to form a DC voltage gradient that compresses the ion beam in the first direction; and/or may comprise successively applying one or more DC voltage to successive electrodes in a direction from the radially outermost electrode towards the radially innermost electrode such that a DC potential barrier travels radially inwards towards the aperture and compresses the ion beam radially.

The DC potential barrier may be applied such that it repeatedly travels from the outermost electrode to the innermost electrode.

The ions may exit the ion trapping region distributed over an initial width in a second direction that is orthogonal to the longitudinal axis and to the first direction; and wherein the method comprises compressing the width in the second direction over which the ions are distributed whilst the ions separate along the longitudinal axis, or after the ions have separated along the longitudinal axis, such that the ions are distributed over a width in the second direction that is smaller than or the same as said initial width in the second direction.

The compressed ion beam may subsequently be transmitted through said aperture.

The ions may be compressed in the second direction in a corresponding manner to the compression in the first direction. The features corresponding to those described herein in relation to compressing the ions in the first direction may be applied to the step of compressing the ions in the second direction. It is also contemplated that ions may be simultaneously compressed in all radial directions relative to the longitudinal axis.

The trapping volume and/or ion separation region may confine ions in a volume that does not have an annular, toroidal or cylindrical cross-section.

Said compressing may be performed in a linear direction.

The ions may be transmitted from the ion separation region directly into a downstream aperture or device, and the ion separation region and the downstream aperture or device may have the same cross-sectional shape.

The cross-sectional shape may be the shape in the plane perpendicular to the longitudinal axis.

The method may comprise detecting or analysing ions that are transmitted through the aperture, e.g. mass analysing such ions.

The compressed ion beam may be subjected to ion analysis and/or further manipulation; such as being directed onto a surface so as to perform Surface Induced Dissociation (SID) of the ions, or directed into a reaction chamber for reacting the ions with other ions or molecules, or directing a laser onto the ions.

It is contemplated that the method of the second aspect may not be limited to including the feature that the exit times are not used in determining the values of a physicochemical property of the ions.

Accordingly, from a third aspect of the present invention there is provided a method of mass spectrometry or ion mobility spectrometry comprising:

accumulating ions in an ion trapping volume;

releasing ions from the ion trapping volume into an ion separation region having a longitudinal axis, wherein the ions exit the ion trapping region distributed over an initial width in a first direction that is orthogonal to the longitudinal axis;

transmitting the ions along a longitudinal axis of the ion separation region such that the ions separate along the longitudinal axis according to a physicochemical property; and compressing the width in the first direction over which the ions are distributed whilst the ions separate along the longitudinal axis, or after the ions have separated along the longitudinal axis, such that the ions are distributed over a width in the first direction that is smaller than or the same as said initial width.

The present invention also proves a spectrometer arranged and configured to perform any of the method steps described herein.

Accordingly, the first aspect of the present invention provides a mass spectrometer or ion mobility spectrometer comprising:

a source of ions;

an ion trapping volume;

an ion separation region having a longitudinal axis; wherein the ion trapping volume is configured such that ions exiting the ion trapping volume are distributed over an initial width in a first direction that is orthogonal to the longitudinal axis; and a controller configured to control the spectrometer to:

transmit ions along the longitudinal axis of the separation region such that the ions separate along the longitudinal axis according to a physicochemical property; and compress the width in the first direction over which the ions are distributed whilst the ions separate along the longitudinal axis such that the ions are distributed over a width in the first direction that is smaller than or the same as said initial width; and transmit the compressed ion beam through an ion acceptance aperture, wherein the initial width of the ion beam in the first direction is greater than the width of the aperture in the first direction, and wherein the ion beam is compressed in the first direction such that when the ions reach the aperture the ion beam has a width in the first direction that is smaller than or the same as the width of the exit aperture in the first direction.

The second aspect of the present invention provides a mass spectrometer or ion mobility spectrometer comprising:

a source of ions;

an ion trapping volume;

an ion separation region having a longitudinal axis; wherein the ion trapping volume is configured such that ions exiting the ion trapping volume are distributed over an initial width in a first direction that is orthogonal to the longitudinal axis; and a controller configured to control the spectrometer to:

transmit ions along the longitudinal axis of the separation region such that the ions separate along the longitudinal axis according to a physicochemical property; and compress the width in the first direction over which the ions are distributed whilst the ions separate along the longitudinal axis, or after the ions have separated along the longitudinal axis, such that the ions are distributed over a width in the first direction that is smaller than or the same as said initial width;

wherein the separated ions exit the ion separation region at different exit times, and wherein the spectrometer does not determine the values of a physicochemical property of the ions from the exit times.

The third aspect of the present invention provides a mass spectrometer or ion mobility spectrometer comprising:

a source of ions;

an ion trapping volume;

an ion separation region having a longitudinal axis; wherein the ion trapping volume is configured such that ions exiting the ion trapping volume are distributed over an initial width in a first direction that is orthogonal to the longitudinal axis; and a controller configured to control the spectrometer to:

transmit ions along the longitudinal axis of the separation region such that the ions separate along the longitudinal axis according to a physicochemical property; and compress the width in the first direction over which the ions are distributed whilst the ions separate along the longitudinal axis, or after the ions have separated along the longitudinal axis, such that the ions are distributed over a width in the first direction that is smaller than or the same as said initial width.

The mass spectrometer may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The mass spectrometer may further comprise a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may comprise a chromatography or other separation device upstream of an ion source. The chromatography separation device may comprise a liquid chromatography or gas chromatography device. The separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

The analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

In order to effect Electron Transfer Dissociation optionally either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

In order to effect Electron Transfer Dissociation, optionally: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

The method disclosed herein enables an extended trapping region to be used to accommodate a large population of ions, thus reducing space charge effects in the trapping region. Ions from this trapping region then enter a mobility separator which compresses the separating packets of ions to smaller volumes with smaller ion populations, suitable for passage through a differential pumping aperture. The act of ion mobility separation in a different direction to the direction of compression facilitates compression of ions to smaller volumes than would otherwise be possible for the entire population contained within the original trapping region due to space charge effects.

The methods disclosed herein help to overcome some of the limitations of space charge effects in ion mobility spectrometers and mass spectrometers, which is an ever increasing issue with brighter ion sources.

BRIEF DESCRIPTION OF THE DRAWINGS

Various embodiments of the present invention will now be described, by way of example only, and with reference to the accompanying drawings in which.

DETAILED DESCRIPTION

Figure 1A:
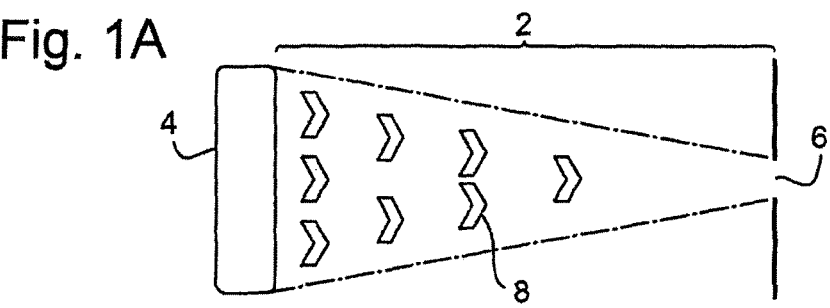
FIG. 1A shows a schematic of a ion mobility spectrometer according to an embodiment of the present invention.

FIG. 1A shows a schematic of an ion mobility separator or spectrometer (IMS) device according to a preferred embodiment of the present invention. The IMS device has an ion mobility separation region 2 arranged between an ion trapping region 4 and an exit aperture 6. The ion trapping region 4 may be elongated in a first direction that is orthogonal to the longitudinal axis of the drift region 2, such that a relatively large volume of ions may be trapped in the elongated trapping region 4. The ion trap 4 may be extended in the first direction such that ions are trapped over a length in the first direction that is longer than the length of the exit aperture 6 in the first direction.

In use, ions are accumulated in the ion trapping region 4 until the desired number of ions are trapped therein. The ions are then pulsed out of the ion trapping region 4 into the separation region 2. The ions travel along the longitudinal axis of the separation region 2 towards the exit aperture 6. As the ions travel through the separation region 2 they separate according to their ion mobility through the separation region 2 and then leave the IMS device through the exit aperture 6. The separation region 2 is filled with gas and the ions separate according to their ion mobility through the gas, as they pass through the separation region 2. The ions therefore pass through the exit aperture 6 in order from high to low ion mobility and may be detected or transmitted to a downstream analyser, such as a mass analyser. As the ions are transmitted through the separation region 2, different ions are accumulated in the ion trapping region 4 from a source of ions arranged upstream of the device. These ions remain trapped in the ion trapping region until they are ready to be pulsed into the separation region 2 in a subsequent packet.

The chevrons 8 in FIG. 1A depict the motion of the ions from the ion trapping region 4 to the exit aperture 6. As the ions are transmitted from the ion trapping region 4 to the exit aperture 6 the ions are compressed in the first direction from a beam having a width in the first direction that is equivalent to the width of the ion trapping region 4, to a width in the first direction that is equivalent to or less than the width of the exit aperture 6. This is depicted in FIG. 1A by the converging dashed lines. As the ions are compressed in the first direction in order to be transmitted through the relatively narrow exit aperture 6, the space-charge effects would be expected to increase, as in conventional arrangements. However, as the ions are separated along the separation region 2 as the compression occurs, this reduces the amount of charge at any given location along the longitudinal axis and so compensates for the increased charge density caused by compression of the ions in the first direction. As such, space-charge effects do not become problematic, even though the ions have been compressed in the first direction in order to exit the narrow exit aperture 6.

Figure 1B:
FIGS. 1B-1D show different plots of the ion charge density along the ion mobility spectrometer at different times.

FIG. 1B shows the amount of charge in the IMS device as a function length along the device at time T=0, when the ions are stored in the trapping region 4, before they have been pulsed into the separation region 2. Peak 10 represents the charge of the ions in the trapping region 4.

Figure 1C:
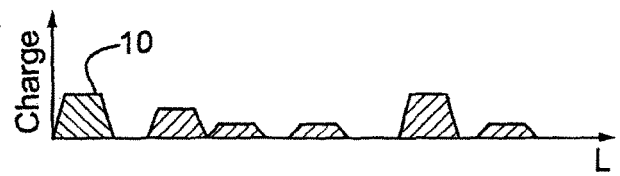

FIG. 1C shows the amount of charge in the IMS device as a function length along the device at a subsequent time T=1, when ions have been released from the trapping region 4 and have separated along the longitudinal axis. The ions have separated into five different groups according to their ion mobilities, wherein the groups are represented by the five peaks that are spaced along the longitudinal axis downstream of peak 10. These ions will continue along the device until they exit the exit aperture 6. As the ions separate in the separation region 2, further ions are accumulated in the ion trapping region 4 from a source of ions upstream of the IMS device. This is illustrated by peak 10 in FIG. 1C.

Figure 1D:
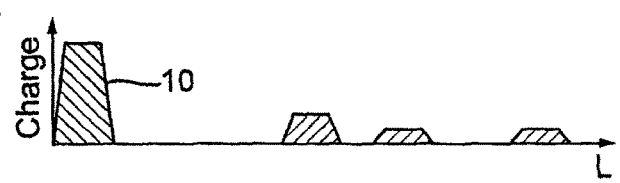

FIG. 1D shows the amount of charge in the IMS device as a function length along the device at time T=2, which is later than T=1. At time T=2 the ions represented by the two rightmost peaks of FIG. 10 have exited the exit aperture 6. The remaining three groups of ions represented by the remaining three peaks that are downstream of peak 10 have separated further along the longitudinal axis of the separation region 2. The leftmost peak 10 has increased in amplitude relative to FIG. 1C, indicating that the ion trapping region 4 has been filled with more ions.

FIGS. 1B to 1D illustrate the principle that the charge density at any given location along the longitudinal axis of the separation region 2 is reduced by separating the ions along the longitudinal axis. This charge reduction is used to compensate for the increase in charge density that is caused by compressing the ions in the first direction. This technique enables ion trapping regions 4 to be used that have a width that is significantly greater than the width of the exit aperture 6, without the ions being subjected to excessive space-charge effects during focusing of the ions towards the exit aperture 6. A greater number of ions can therefore be pulsed into the separation region 2 at one time. As the technique is able to compress the ions without excessive space-charge effects, the exit aperture 6 is able to remain relatively small. This may be useful, for example, if the exit aperture 6 forms a differential pumping aperture between two regions of different pressures. As the aperture 6 may remain of small size, the rate at which gas flows between the two regions separated by the aperture is relatively low and so relatively low power pumps may be used to evacuate these regions.

Figure 2:
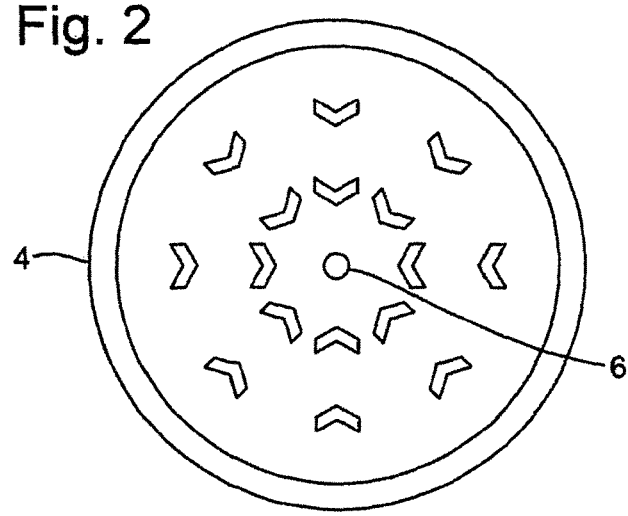
FIG. 2 shows a schematic of another embodiment wherein ions are compressed radially inwards as they travel along the separation region of the ion mobility spectrometer.

FIG. 2 shows a schematic of an end view of an embodiment of the present invention that operates in the same manner as described above with reference to FIG. 1. In this embodiment the ion trapping region 4 pulses a substantially circular beam of ions along the longitudinal axis of the separation region 2 towards the exit aperture 6, wherein the exit aperture 6 has a smaller diameter than the beam of ions at the time that the ion beam is pulsed out of the ion trapping region 4. The exit aperture 6 is provided in a wall of the device and has a plurality of ring electrodes arranged concentrically around the exit aperture 6. Electrical potentials are applied to the ring electrodes to as to provide a force on the ions that compresses the ion beam radially in a direction towards the central axis of the aperture 6.

For example, DC voltages may be applied to the ring electrodes to form a DC voltage gradient that urges ions radially inwards towards the centre of the exit aperture 6. Alternatively, a DC voltage may be applied successively to the ring electrodes in a direction from the outermost ring electrode towards the innermost ring electrode. This creates a potential barrier that travels radially inwards towards the exit aperture 6 and drives the ions radially inwards. The travelling potential may be applied such that it repeatedly travels from the outermost electrode to the innermost electrode. Whether the radial driving force is provided by a static DC gradient or by a travelling potential, an RF potential may be applied to the wall or RF potentials may be applied to the ring electrodes so as to urge ions that approach close to the wall in a direction away from the wall along the longitudinal axis. This prevents ions from impacting the wall or ring electrodes rather than being transmitted through the exit aperture 6.

The embodiment of FIG. 2 operates in the same manner as that described in relation to FIG. 1. Ions are pulsed out of the ion trapping region 4 and separate along the longitudinal axis according to their ion mobilities. The voltages applied to the ring electrodes cause the compression of the ion beam in the first direction (i.e. the radial direction).

In all embodiments of the present invention, the ions may be urged along the longitudinal axis of the separation region 2 towards the exit aperture 6. One or more static electric fields and/or time-varying electric fields may be used to separate the ions along the longitudinal axis. This may be achieved, for example, by applying a DC voltage gradient along the longitudinal axis of the separation region 2. Alternatively, or additionally, a DC potential barrier may be traveled along the longitudinal axis of the separation region 2 so as to drive ions along it and towards the exit aperture 6. This may be achieved by successively applying one or more voltages to successive electrodes arranged along the longitudinal axis of the separation region 2.

Linear and/or non-linear electric fields may be used to separate the ions along the longitudinal axis.

Although the present invention has been described with reference to embodiments, it will be understood by those skilled in the art that various changes in form and detail may be made without departing from the scope of the invention as set forth in the accompanying claims.

For example, although the ions have been described as being separated according to their ion mobility along the longitudinal axis, they may be separated according to a different physicochemical property instead, such as mass-to-charge ratio.

It will be appreciated that the exit aperture 6 may be circular, but may be another non-circular shape. For example, the aperture 6 may be significantly bigger in one dimension than another, e.g. may be slot shaped, oval or rectangular. The larger dimension may be in the direction of ion compression or in another direction.

The ion separation region 2 may have a curved or circular shaped cross-section through the longitudinal axis, as in the embodiment of FIG. 2. Alternatively, the cross-section may be non-circular. For example, the separation region 2 may have a larger dimension in one direction orthogonal to the longitudinal axis, as compared to another direction orthogonal to the longitudinal axis. Said one direction may also be orthogonal to said another direction. For example, the cross-sectional shape may be oval or rectangular.

Both the exit aperture 6 and cross-sectional shape of the separation region 2 may be larger in one dimension than another, as described above. In such embodiments, the larger dimension of the separation region may correspond (i.e. be parallel) to the larger dimension of the exit aperture.

Ions may be compressed in the first direction by applying RF and/or DC voltages to electrodes of the device.

The invention claimed is:

1. A method of mass spectrometry or ion mobility spectrometry comprising:
   accumulating ions in an ion trapping volume;
   releasing ions from the ion trapping volume into an ion separation region having a longitudinal axis, wherein the ions exit the ion trapping region distributed over an initial width in a first direction that is orthogonal to the longitudinal axis;
   pulsing the ions along a longitudinal axis of the ion separation region such that the pulsed ions separate as they travel along the longitudinal axis according to a physicochemical property;
   compressing the width in the first direction over which the ions are distributed whilst the ions separate along the longitudinal axis such that the ions are distributed over a width in the first direction that is smaller than said initial width; and
   transmitting the compressed ion beam through an ion acceptance aperture, wherein the initial width of the ion beam in the first direction is greater than the width of the aperture in the first direction, and wherein the ion beam is compressed in the first direction such that when the ions reach the aperture the ion beam has a width in the first direction that is smaller than or the same as the width of the aperture in the first direction.

2. The method of claim 1, wherein the separated ions exit the ion separation region at different exit times, and wherein the exit times are not used in determining the values of a physicochemical property of the ions.

3. The method of claim 1, wherein the ions are transmitted through the ion separation region with different transit or drift times, and wherein the transit or drift times are not used in determining the values of a physicochemical property of the ions.

4. The method of claim 2, wherein the exit times, transit times or drift times are not used to determine the ion mobilities of the separated ions.

5. The method of claim 1, wherein said compressing begins in the ion separation region within a distance x cm of the location at which ions are released from the ion trapping volume, wherein x is selected from the group consisting of: $\leq 100$; $\leq 90$; $\leq 80$; $\leq 70$; $\leq 60$; $\leq 50$; $\leq 40$; $\leq 30$; $\leq 20$; $\leq 10$; $\leq 5$; $\leq 4$; $\leq 3$; $\leq 2$; and $\leq 1$.

6. The method of claim 1, wherein the ions exit the ion trapping volume directly into a region in which the ions are compressed in the first direction such that the ions begin to be compressed in the first direction immediately after they exit the ion trapping volume.

7. The method of claim 1, wherein the ion beam is compressed to progressively narrower widths in the first direction as the ions travel along the longitudinal axis of the separation region.

8. The method of claim 1, comprising accumulating ions in the ion trapping volume and then releasing, pulsing or ejecting the ions from the ion trapping volume into the separation region.

9. The method of claim 1, wherein the ions are separated along the longitudinal axis according to ion mobility.

10. The method of claim 1, comprising urging ions along the longitudinal axis of the separation region away from the ion trapping volume.

11. The method of claim 1, wherein ions are compressed in the first direction by RF and/or DC potential barriers.

12. The method of claim 1, wherein the aperture is a differential pumping aperture that is formed in a wall separating two regions maintained at different pressures.

13. The method of claim 1, wherein the aperture is provided in a wall and a plurality of electrodes are arranged on the wall radially outward of the aperture in at least the first direction, wherein the method comprises applying DC and/or AC voltages to said electrodes so as to compress the ions in the first direction.

14. The method of claim 13, comprising applying RF potentials to said electrodes so as to repel ions and prevent them contacting the wall.

15. The method of claim 13, wherein the electrodes comprise a plurality of closed-loop electrodes arranged concentrically around and radially outward of the aperture.

16. The method of claim 13, comprising applying different DC voltages to different ones of said electrodes so as to form a DC voltage gradient that compresses the ion beam in the first direction; and/or
  comprising successively applying one or more DC voltage to successive electrodes in a direction from the radially outermost electrode towards the radially innermost electrode such that a DC potential barrier travels radially inwards towards the aperture and compresses the ion beam radially.

17. The method of claim 1, wherein the ions are transmitted from the ion separation region directly into a downstream aperture or device, and wherein the ion separation region and the downstream aperture or device have the same cross-sectional shape.

18. A method of mass spectrometry or ion mobility spectrometry comprising:
  accumulating ions in an ion trapping volume;
  releasing ions from the ion trapping volume into an ion separation region having a longitudinal axis, wherein the ions exit the ion trapping region distributed over an initial width in a first direction that is orthogonal to the longitudinal axis;
  transmitting the ions along a longitudinal axis of the ion separation region such that the ions separate along the longitudinal axis according to a physicochemical property; and
  compressing the width in the first direction over which the ions are distributed whilst the ions separate along the longitudinal axis, such that the ions are distributed over a width in the first direction that is smaller than said initial width;
  wherein the separated ions exit the ion separation region at different exit times, and wherein the exit times are not used in determining the values of a physicochemical property of the ions.

19. The method of claim 18, further comprising transmitting the compressed ion beam through an ion acceptance aperture, wherein the initial width of the ion beam in the first direction is greater than the width of the aperture in the first direction, and wherein the ion beam is compressed in the first direction such that when the ions reach the aperture the ion beam has a width in the first direction that is smaller than or the same as the width of the aperture in the first direction.

20. A mass spectrometer or ion mobility spectrometer comprising:
  a source of ions;
  an ion trapping volume;
  an ion separation region having a longitudinal axis; wherein the ion trapping volume is configured such that ions exiting the ion trapping volume are distributed over an initial width in a first direction that is orthogonal to the longitudinal axis; and
  a controller configured to control the spectrometer to:
  transmit ions along the longitudinal axis of the separation region such that the ions separate along the longitudinal axis according to a physicochemical property; and:
  (i) compress the width in the first direction over which the ions are distributed whilst the ions separate along the longitudinal axis such that the ions are distributed over a width in the first direction that is smaller than said initial width; and
    transmit the compressed ion beam through an ion acceptance aperture, wherein the initial width of the ion beam in the first direction is greater than the width of the aperture in the first direction, and wherein the ion beam is compressed in the first direction such that when the ions reach the aperture the ion beam has a width in the first direction that is smaller than or the same as the width of the aperture in the first direction; or
  (ii) compress the width in the first direction over which the ions are distributed whilst the ions separate along the longitudinal axis, such that the ions are distributed over a width in the first direction that is smaller than said initial width;
    wherein the separated ions exit the ion separation region at different exit times, and wherein the spectrometer does not determine the values of a physicochemical property of the ions from the exit times.

* * * * *